United States Patent [19]

Hammond et al.

[11] Patent Number: 5,149,807
[45] Date of Patent: Sep. 22, 1992

[54] OXAZINE LASER DYES

[75] Inventors: Peter R. Hammond, Livermore; George F. Field, Danville, both of Calif.

[73] Assignee: The United States of America, as represented by the United States Department of Energy, Washington, D.C.

[21] Appl. No.: 761,559

[22] Filed: Sep. 18, 1991

[51] Int. Cl.$^5$ .................. C07D 498/14; C07D 498/22
[52] U.S. Cl. ...................................... 544/99
[58] Field of Search ........................................ 544/99

[56] References Cited

U.S. PATENT DOCUMENTS

| | | | |
|---|---|---|---|
| 4,026,898 | 5/1977 | Henry et al. | 260/288 |
| 4,202,981 | 5/1980 | Hammond et al. | 546/82 |
| 4,622,400 | 11/1986 | Hammond | 546/179 |
| 4,945,176 | 7/1990 | Hammond et al. | 549/227 |

FOREIGN PATENT DOCUMENTS 3011154  10/1981  Fed. Rep. of Germany .
2026014   7/1979  United Kingdom .

OTHER PUBLICATIONS

Clapp, R. C., et al., "Chemotherapeutic Dyes, IV. Phenoxazines and Benzo[a]phenoxazines", J. Am. Chem. Scoc. 74, 1989 (1952).
Psaar, H. and Heitzer, H., "Note on the constitution of the oxazine dyes C.I. Basic Blue 3 and C.I. Basic Blue 4," Chem. Ber. 102, 3603–3604 (1969).
Moores, M. S. et al., "The Structure of Basic Blue, 3,7-Bis(diethylamino)phenazoxonium Chloride," J. Hertercycl. Chem. 6, 755 (1969).
Mohlau, R., "About Oxazine Dyes," Chem. Ber. 25, 1022 (1892).
Le Bris, M-T., "Synthesis of New Fluorescent Dyes in the Benzoxazinone Series: Aminobenzoxazinones with a Rigidized Structure," Heterocycl. Chem. 26, 429 (1989).

Primary Examiner—Mukund J. Shah
Assistant Examiner—Philip I. Datlow
Attorney, Agent, or Firm—Miguel A. Valdes; Roger S. Gaither; William R. Moser

[57] ABSTRACT

New oxazine compounds useful as dye laser media in solution, are superiior to prior art materials. The oxazine dyes useful when pumped by the 578.2 nm copper line to operate in the 700–800 nm range are described by formula I

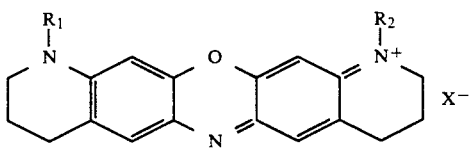

and formula II 5 Claims, 1 Drawing Sheet

OXAZINE LASER DYES

The U.S. Government has rights in this invention pursuant to Contract No. W-7405-ENG-48 between the U.S. Department of Energy and University of California for the operation of the Lawrence Livermore National Laboratory.

TECHNICAL FIELD

The present invention relates generally to dye compositions useful in laser applications, and more specifically this invention relates to oxazine compositions used as laser dyes.

BACKGROUND OF THE INVENTION

Dye solutions useful as laser active liquid organic media have been the subject of substantial research effort because the lasers are tunable. These laser active liquid media are of interest because they are generally more economical than solid or gaseous materials; they are not prone to defects observed with solid materials, and generally provide a wider range of selections. A review of the research in this area can be obtained by reference to the following patents: U.S. Pat. No. 4,026,898; U.S. Pat. No. 4,202,982; U.S. Pat. No. 4,622,400 and U.S. Pat. No. 4,945,176.

The present invention provides novel oxazine compositions which are particularly useful in laser dye applications. These novel compositions are used in laser operation in the 700-800 nm wavelength range when excited by the 578.2 nm copper line.

SUMMARY OF THE INVENTION

Oxazine salts, particularly, but not exclusively, the fluoborate, are provided as laser dyes and are advantageous in such application because the dyes are stable under laser operation conditions and do not impair the optics of the amplifier windows in the laser.

According to the present invention, the following two compositions are useful as laser dyes:

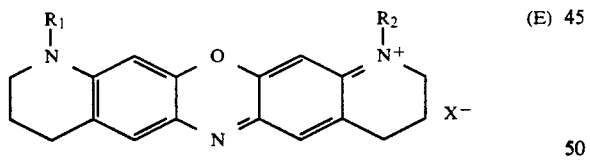

(E)

wherein $R_1$ and $R_2$ are independently selected from substituent groups consisting of linear and branched alkyl and fluoroalkyl groups of 1 to 10 carbon atoms, and wherein $X^-$ is an anion; and,

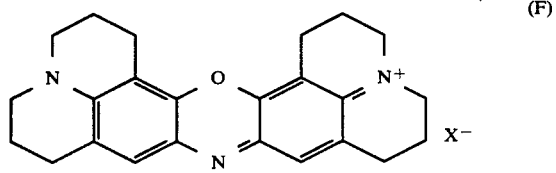

(F)

wherein $X^-$ is an anion.

For both dyes (E) and (F), the preferred anion $X^-$ is selected from the group consisting of fluoborate, chloride, perchlorate and trifluoromethanesulfonate.

DETAILED DESCRIPTION OF THE INVENTION

Figure 1:
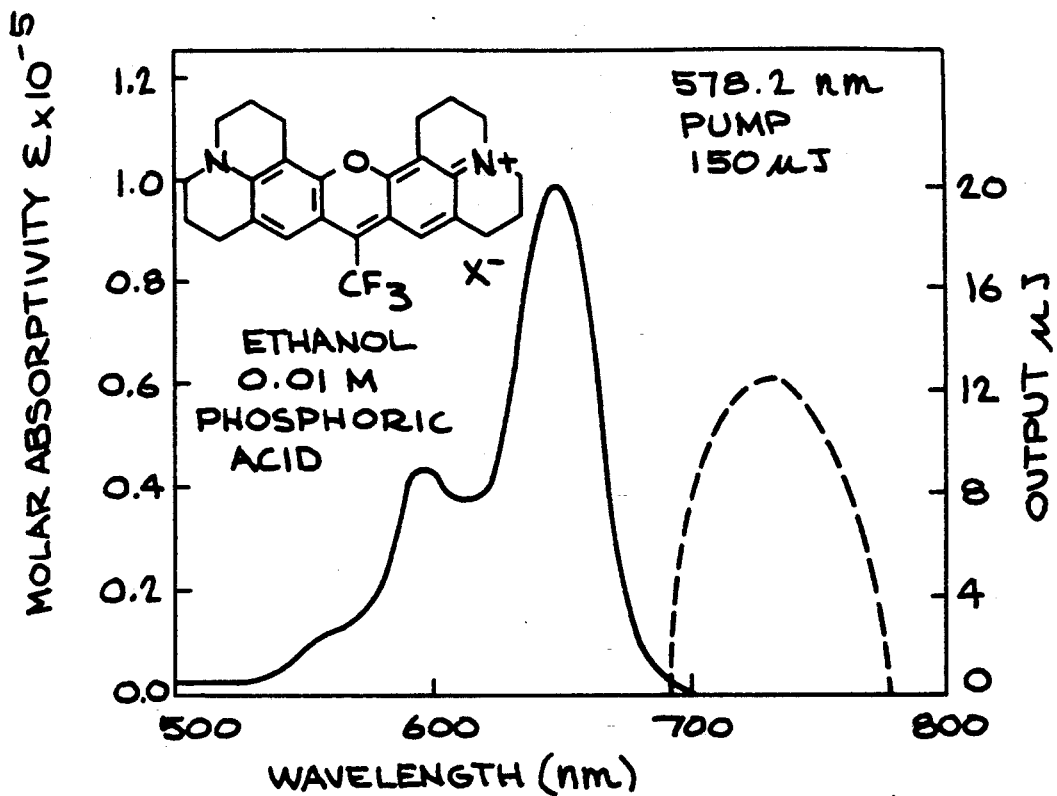
FIG. 1 is a plot of the oscillator performance of LD 700 2,3,6,7,12,13,16,17-octahydro-9-trifluoromethyl)-1H,5H, 11H, 15H-xantheno[2,3,4-ij:5,6,7-i'j'] diquinolizin-18-ium perchlorate, a prior art laser dye, dissolved in acidified ethanol, pumped at 578.2 nm. See Example 3.

Dyes that can be pumped by the copper vapor laser to operate in the 700-800 nm region are the green-pumped (510.6 nm) Pyridine-1(A) 2-[4-[4-(dimethylamino)pheny]-1,3-butadienyl]-1-ethyl-pyridinium perchlorate and Pyridine-2 (B) 4-[4-[4-(dimethylamino)-phenyl]-1,3-butadienyl]-1-ethyl-pyridinium perchlorate, and the yellow-pumped (578.2 nm) LD 700 (C).

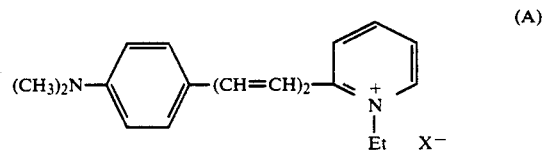

(A)

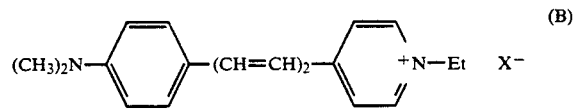

(B)

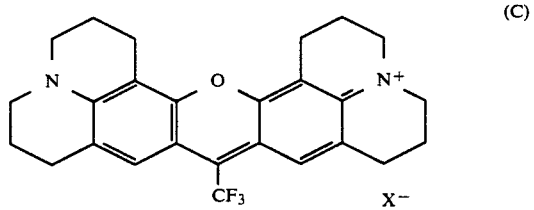

(C)

A green-pumped dye amplifier containing an ethanol solution of Pyridine-2 (B) gave only 5% conversion. Yellow-pumped LD 700 operation, although more efficient (25-30%) than Pyridine-2, resulted in the degradation of the laser silica output window, possibly caused by the action of dye decomposition products on the silica. Use of LD 700 is further complicated by its requirements for acid conditions. There is presently no good dye option for this wavelength range which does not have these significant drawbacks.

The oxazine chromophore is chemically similar to, and has spectra displaced about 90 nm to the red of the rhodamines. An aminoalkyl constrained dye (D), chemically related to rhodamine 6G, is sold commercially (Exciton - LD 690; Eastman - Oxazine 4). The tetraethyl derivative [3,7-bis(diethylamino)-phenoxazonium salt] is also known under the names Basic Blue 3, Oxazine I (Eastman) and Oxazine 725 (Exciton).

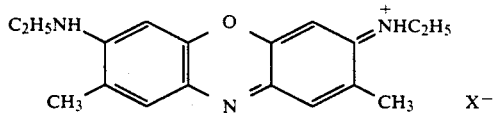

(D)

We have determined that another oxazine compound, 3,4,8,9,10,11-hexahydro-1,11-dimethyl-2H-dipyrido[3,2-b:2',3'-i]-phenoxazinium fluoborate, dye (E), in ethanol has an absorption maximum at 649 nm and lases in the 690–760 nm region under 578.2 nm excitation.

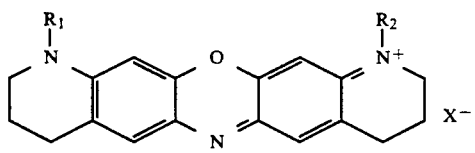

(E)

Unlike LD 700, dye (E) does not require acid conditions for stability. Dye (E) will not degrade laser amplifier output windows.

Other oxazine compositions, such as 2,3,6,7,12,13,16,17-octahydro-1H,5H, 11H, 15H-diquinolizino[1,9-bc:1',9'-hi]phenoxazin-4-ium fluoborate, dye (F), can be easily synthesized from the aminophenol intermediates used to prepare the rhodamine-class dyes. These oxazine compounds can be pumped efficiently by the krypton-ion 647 nm line for continuous wave operation.

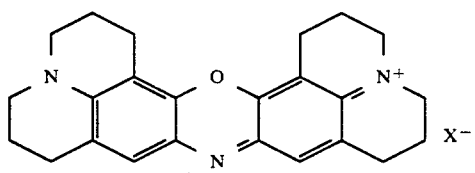

(F)

The oxazine compounds (E) and (F) are nitrogen dialkyl substituted and ring constrained. Thus, they are hydrolytically and photolytically stable dyes at the wavelength of interest with optimized fluorescence quantum yield.

Synthesis of oxazines according to the present invention is briefly depicted below for the case of dye (E). A 1,3-aminophenol (G) or derivative (H) is nitrosated to give the nitroso compound (K) which need not be isolated. In the most direct version, this nitroso compound (K) is condensed with another mole of aminophenol (G) to give the oxazine (E). A modern variant nitrosates a 1,3-aminoether (H) and condenses the product with an aminophenol (G). (M. S. Moores, W. J. Balon, and C. W. Maynard, Jr., "The structure of Basic Blue 4. 3,7-Bis(diethylamino)phenazoxonium chloride" J. Heterocycl. Chem. 6, 755 (1969). R. Mohr and R. Neeb, "Zinc chloride complex compounds and their use as phenoxazine dye intermediates." Ger. Off. DE 3,011,154 (Oct. 1981.) The later authors used m-aminophenol, nitroso-m-methoxyamine and zinc chloride in ethanol, and the zinc double salt precipitated. This salt was warmed and carefully neutralized with aqueous sodium bicarbonate to give the hydrochloride.

Another approach to synthesis of dye (E) is the condensation of the nitroso compound with a 1,3-diamine with loss of dimethylamine. (P. Moser, Ciba-Geigy Patents. Chem. Abs. 101:193677m; ibid, 93:241194s; ibid. 93:73772h.) There are also some routes involving (L) which require a subsequent oxidation to form the final ring system, (H. Psaar and H. Heitzer, "Note on the constitution of the oxazine dyes C. I. Basic Blue 3 and C. I. Basic Blue 4," Chem. Ber. 102, 3603–3604 (1969). R. C. Clapp, J. H. Clark, J. P. English, C. E. Fellows, R. E. Grotz, and R. G. Shepherd, "Chemotherapeutic dyes. IV. Phenoxazines and benzo[a]phenoxazines, " J. Am. Chem. Soc. 74, 1989 (1952)), but reported yields for these routes are low.

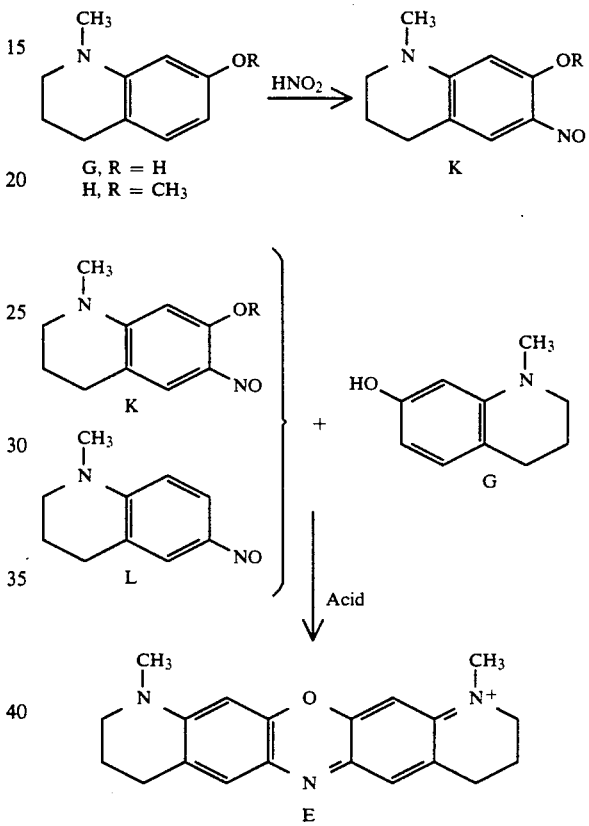

EXPERIMENTAL EXAMPLES

EXAMPLE 1

Dye Properties in 190 Proof Ethanol

Dye (E). 3,4,8,9,10,11-Hexahydro-1,11-dimethyl-2H-dipyrido[3,2-b:2',3'-i]-phenoxazinium fluoborate (0.5 H$_2$O). M416.2; $\epsilon_{578.2}=0.253\times 10^5$; $\epsilon_{649}$ (the absorption maximum) = 1.204 × 10$^5$.

| Solubility: | 5° C. | 3.75 g/L |
|---|---|---|
| | 78.5° C. | 50 g/L |

EXAMPLE 2

Dye Properties in 190 Proof Ethanol

Dye (F). 2,3,6,7,12,13,16,17-Octahydro-1H,5H,11H,15H-diquinolizino[1,9-bc:1',9'-hi]phenoxazine-4-ium fluorborate H$_2$O. M477.3; $\epsilon_{578.2}=0.140\times 10^5$; $\epsilon_{668}$ (the absorption maximum) = 1.138 × 10$^5$.

EXAMPLE 3

Figure 2:
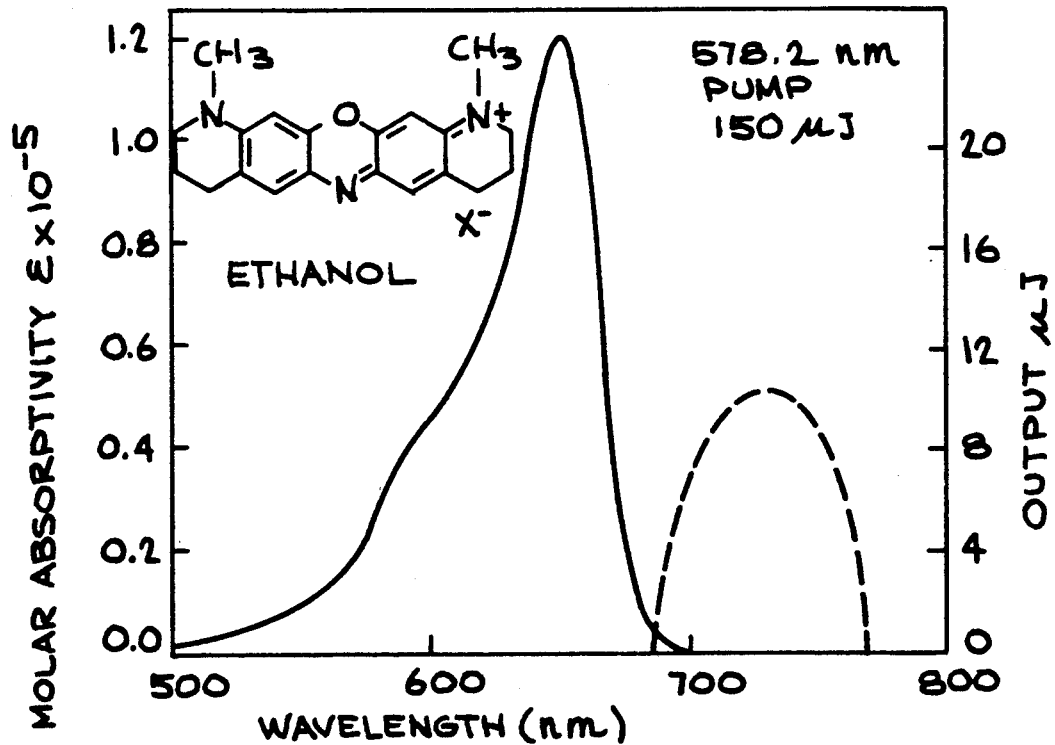
FIG. 2 is a plot of the performance of a dye according to formula (E) 3,4,8,9,10,11-hexahydro-1,11-dimethyl-2H-dipyrido[3,2-b:2',3'-i]-phenoxazinium fluoborate dissolved in ethanol, pumped at 578.2 nm under identical conditions. See Example 3.

Oscillator performances for LD 700 and Dye (E) in ethanol are shown in FIGS. 1 and 2, respectively. Dye concentration was chosen to give 90% absorbance at the 578.2 nm pump wavelength for a 300 μ depth. The oscillator were tweaked for each position of measurement. The tuning ranges (688–765 nm for dye (E) vs 698–778 nm for LD 700), peak wavelengths (731 nm vs 731 nm) and peak outputs (10.5 μJ vs 12.4 μJ) were similar.

Dye (E) is an effective laser dye although its oscillator performance is slightly inferior to LD 700 (about 15%). Unlike LD 700, it does not require acid conditions for stability and it does not impair amplifier output window optics.

The oxazine dye compositions of the present invention are simple to make from the aminophenol intermediates used to prepare the rhodamine-class dyes, thus, e.g., dye (E) is amenable to commercial production. (U.S. Pat. No. 4,622,400.) Also, it should be pumped efficiently by the krypton-ion 647 nm line for continuous wave operation.

SYNTHESIS EXPERIMENTS

EXAMPLE 4

1,2,3,4-Tetrahydro-1-methyl-6-nitroso-7-hydroxyquinoline hydrochloride.

A mixture of 24.5 g (0.15 mol) of 1-methyl-1,2,3,4-tetrahydro-7-hydroxyquinoline, 75 ml of water and 75 ml of concentrated hydrochloric acid was stirred and cooled in an ice bath to 5°. To this mixture was added dropwise during 40 minutes a solution of 12.42 g (0.18 mol) of sodium nitrite in 50 ml of water while maintaining the temperature between 3 to 5° C. It was occasionally necessary to add a few ml of ether to control foaming. When the addition was complete, the reaction mixture was stirred for 40 min in the ice bath. The solid was collected and rinsed with 2N hydrochloric acid and with ether. It was recrystallized from 700 ml of 2.4 N hydrochloric acid to give 28.7 g (84%) of crude product as brown needles.

EXAMPLE 5

Dye (E).
3,4,8,9,10,11-Hexahydro-1,11-dimethyl-2H-dipyrido[3.2-b:2',3'-i]-phenoxazinium fluorborate.

To a solution of 8.2 g (50 mmol) of 7-hydroxykairoline in 100 ml of ethanol and 10 ml of 60% fluorobic acid stirred and heated to 75° in an oil bath was added in portions during 45 minutes 12 g (53 mmol) of 1-methyl-1,2,3,4-tetrahydro-6-nitroso-7-hydroxyquinoline hydrochloride. The reaction mixture was stirred and heated under reflux for 1.7 hr, cooled slightly, treated with 5 ml of 51% fluoboric acid and cooled in the refrigerator for 3 hrs. The solid was collected to give 9.48 g(47%) of crude product. The mother liquor on standing overnight deposited a further 0.81 g of product for a total yield of 51%. The product from this experiment and than from a similar one were combined to give 21.38 g which was recrystallized from 500 ml of ethanol to give 16.2 g of purified compound $C_{20}H_{22}N_3OBF_4.0.5H_2O$ (76% recovery). The material showed one spot by thin layer liquid chromatography on silica gel (methylene chloride/methanol/actic acid -45/5/1).

An analytical sample prepared by recrystallization from ethanol was obtained as green plates with a yellow sheen, mp 210–220° C. Analysis calculated for $C_{20}H_{22}N_3OBF_4.O.5H_2O$: C,57.73; H, 5,57; N,10.10. Found : C,57.80; H,5.54; N,10.09.

EXAMPLE 6

7-Nitroso-8-hydroxyjulolidine hydrochloride.

A mixture of 9.47 g (50 mmol) of 8-hydroxyjulolidine, 120 ml of methanol, 40 ml of water and 20 ml of concentrated hydrochloric acid was stirred and cooled in a salt/ice bath to 2° C. A small amount of precipitate formed. To this mixture was added a mixture of 37 ml (57 mmol) of 10% aq. sodium nitrite solution and 63 ml of methanol dropwise during 5 min. A heavy precipitate formed and the temperature rose to 4°. The reaction mixture was kept in the ice bath for 2 hr. The solid was collected, rinsed with cold 2.4 N hydrochloric acid, and air dried overnight to give 14.46 g (theory 12.74 g) of crude product. This material and that from an experiment of the same scale (16.19 g) were combined and recrystallized from 750 ml of 2.4 N hydrochloric acid using a coarse sintered-glass funnel to clarify the solution. There was obtained 22.33 g (88%) of product.

EXAMPLE 7

Dye (F).
2,3,6,7,12,13,16,17-Octahydro-1H,5H,11H,15H-diquinolizino[1,9-bc:1',9'-hi]phenoxazin-4-ium fluoborate.

To a solution of 0.95 g (5 mmol) of 8-hydroxyjulolidine in 25 ml of ethanol and 1 ml of 2.4 M hydrochloric acid stirred in an oil bath was added 1.3 g (5.2 mmol) of 8-hydroxy-7-nitrosojulolidine during 30 minutes while the temperature was raised from 40° to 60° C. A thin layer chromatograph (acetic acid/methanol/methylene chloride -1/5/45, on silica) fifteen minutes later showed the reaction product to consist almost entirely of a fast purple spot. The reaction mixture was heated to 60° C. (internal) for 5.5 hr. Thin liquid chromatography showed mainly the slower blue spot of dye (F). The reaction mixture was rinsed into an Erlenmeyer flask with 2 ml of ethanol, treated with 2 ml of 50% fluorobic acid and put in the refrigerator overnight. The product had oiled out. The mixture was seeded, warmed, scratched and recooled. From the mixture was collected 0.7 g (30%) of crude brown crystalline material. Recrystallization from 35 ml of water gave 0.4 g of product. This material was combined with similar and recrystallized twice more from water to give green prisms, mp 260–270° C. Analysis calculated for $C_{24}H_{26}N_3OBF_4.H_2O$: C,60.39; H,5.91; N,8.80. Found: C,60.38; H,5.66; N,8.75.

While the present invention has been described with reference top particularly preferred embodiments, these descriptions are not intended to limit the scope of the appended claims. Those of ordinary skill in the art will appreciate that variations and other embodiments are possible, which although out described, are within the scope and spirit of the invention.

What is claimed is:

1. A compound of the formula

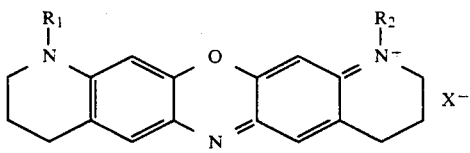

wherein $R_1$ and $R_2$ are independently selected from the substituent groups consisting of linear and branched alkyl and fluoroalkyl groups of 1 to 10 carbon atoms, and wherein $X^-$ is an anion.

2. A compound according to claim 1 wherein said anion $X^-$ is selected from the group consisting of chloride, fluoborate, perchlorate and trifluoromethanesulfonate.

3. A compound according to claim 1 wherein said anion $X^-$ is a fluoborate and $R_1$ and $R_2$ are methyl groups.

4. A compound of the formula

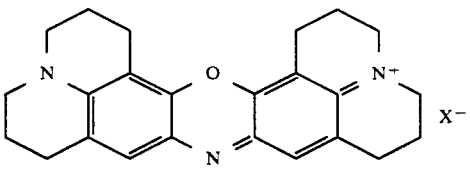

wherein $X^-$ is an anion.

5. A compound according to claim 4 wherein said anion $X^-$ is selected from the group consisting of chloride, and fluoborate, perchlorate and trifluoromethanesulfonate.

* * * * *